United States Patent [19]

Cosquer et al.

[11] Patent Number: 5,141,962
[45] Date of Patent: Aug. 25, 1992

[54] AMINE COMPOUNDS

[75] Inventors: Philippe Cosquer, Saint-Denis; Francoise Delevallee, Fontenay sous Bois; Serge Droux, Aulnay sous Bois; Michel Fortin, Paris; Francis Petit, Bondy, all of France

[73] Assignee: Roussel Uclaf, Paris, France

[21] Appl. No.: 516,045

[22] Filed: Apr. 27, 1990

[30] Foreign Application Priority Data

Apr. 28, 1989 [FR] France .................. 89-05649

[51] Int. Cl.$^5$ .................. A61K 31/135; C07C 215/52
[52] U.S. Cl. .................. 514/654; 564/374
[58] Field of Search .................. 564/374; 514/654

[56] References Cited

U.S. PATENT DOCUMENTS 4,130,658 12/1978 Nedelec et al. .................. 564/374
4,175,136 11/1979 Nedelec et al. .................. 564/374

FOREIGN PATENT DOCUMENTS 1037655 8/1966 United Kingdom .................. 564/374
2126213 3/1984 United Kingdom .................. 564/374

OTHER PUBLICATIONS

Nedelec et al, "Synthesis and Study of the Dopaminergic Activity of Di(Phenylethyl)amine Derivatives", Calif. 90 168185w (1979).

Primary Examiner—Richard L. Raymond
Attorney, Agent, or Firm—Bierman and Muserlian

[57] ABSTRACT

A compound selected from the group consisting of N-pentyl-N-phenethyl-3-hydroxyphenethylamine of the formula

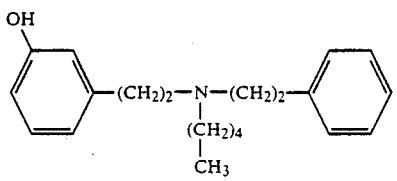

and its non-toxic, pharmaceutically acceptable acid addition salts having a remarkably dissociated antagonist affinity for kappa opiate receptor.

6 Claims, No Drawings

AMINE COMPOUNDS

STATE OF THE ART

Related prior art includes U.S. Pat. No. 4,242,355 and U.S. Pat. No.4,130,658 and U.S. patent application Ser. No. 086,996 filed Aug 19, 1987.

OBJECTS OF THE INVENTION

It is an object of the invention to provide the novel compound of formula I and its non-toxic, pharmaceutically acceptable acid addition salts.

It is another object of the invention to provide compositions with a dissociated antagonistic affinity for kappa opiate receptors and to a novel method for inducing said affinity in warm-blooded animals.

These and other objects and advantages of the invention will become obvious from the following detailed description.

THE INVENTION

The novel products of the invention are N-pentyl-N-phenethyl-3-hydroxyphenethylamine and its non-toxic, pharmaceutically acceptable acid addition salts.

Examples of suitable acids for the formation of the acid addition salts are inorganic acids such as hydrochloric acid, hydrobromic acid, hydriodic acid, nitric acid, sulfuric acid and phosphoric acid, organic acids such as acetic acid, formic acid, benzoic acid, maleic acid, fumaric acid, succinic acid, tartaric acid, citric acid, oxalic acid, glyoxylic acid, aspartic acid, alkanesulfonic acids such as methane sulfonic acid and arylsulfonic acids such as benzene sulfonic acid.

The novel process of the invention for the preparation of the compound of formula I comprises demethylating a compound of the formula

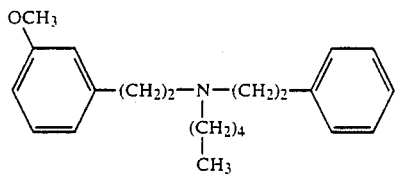

to obtain the compound of formula I which can be optionally salified with an approximately stoichiometric amount of an acid to form the acid addition salt. Preferably, the demethylation is efffected at reflux with concentrated hydrobromic acid.

The novel compositions of the invention having a dissociated antagonistic affinity for kappa opiate receptors comprises an effective amount of the compound of formula I and its non-toxic, pharmaceutically acceptable acid addition salts and an inert pharmaceutical carrier. The compositions may be in the form of tablets, dragees, gelatin capsules, granules, suppositories and injectable solutions or suspensions.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions also have a weak affinity for the mu opiate receptor and practically no affinity for the $D_2$ dopaminergic receptor. The compositions are useful in intensive treatment with an agonist product of the kappa opiate receptor necessitating an interruption for reasons, for example, of overdoses. Such a type of kappa agonist composition is described, for example, in French Patent No. 2,603,035 and is used notably for combating pain of various origins, for example, pain of a muscular, articular or nervous nature. Another example of the kappa agonist is the product: U 504 88 which has in addition to the analgesic property, a diuretic property.

The effect of the kappa antagonist product of the invention is to specifically displace the agonist product by competition at the level of the kappa receptor, thereby playing the role of an antidote. In this way, the compositions can, for example, exert an antagonistic effect vis-a-vis the analgesic or diuretic activity of a kappa agonist.

Also, the compositions are useful as a specific pharmacological tool. This property makes them quite particularly valuable for laboratory experiments which require a high specificity in the reference product used, which the reference products best known as antagonists of the kappa opiate receptor do not possess, such as NALOXONE or MR2266 which recognize, in particular, the mu opiate receptor. Therefore, an object of the invention is also the use of the product of formula I as defined above as a means of study, the assay and localization of kappa opiate receptors.

Another object of the invention is the use of N-pentyl-N-phenethyl-3-hydroxyphenethylamine and its salts for the treatment of overdoses of an agonist product of the kappa opiate receptor in warm-blooded animals, including humans, by administering the compounds of the invention. The compounds may be administered orally, rectally or parenterally and the usual daily dose is 0.66 to 2.66 mg/kg depending upon the method of administration and the condition treated.

The compound of formula II is a novel compound and is an object of the invention. The compound of formula II can be prepared by reacting a compound of the formula

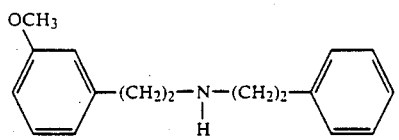

with a halide of the formula

Hal—(CH₂)₄—CH₃    IV wherein Hal is chlorine, bromine or iodine to obtain the desired product of formula II. The preparation of the product of formula III is described in French Patent No. 2,356,417.

In the following examples there are described several preferred embodiments to illustrate the invention. However, it should be understood that the invention is not intended to be limited to the specific embodiments.

EXAMPLE 1

N-pentyl-N-phenethyl-3-hydroxyphenethylamine 13.4 g of N-phenethyl-3-methoxyphenethylamine hydrobromide [prepared as in French patent No. 2,356,417, Example 1], 200 ml of acetone, 22 ml of pentyl iodide and 29.3 g of potassium carbonate were refluxed for 4 hours and were vacuum filtered. The filter was washed with acetone and the filtrate was concentrated to dryness under reduced pressure. The 30 g of residue were chromatographed on silica (eluant: cyclohexane - ethyl acetate 7-3) to obtain 11.4 g of pure N-pentyl-N-phenethyl-3-methoxy-phenethylamine.

A mixture of 6.7 g of the said product in 40 ml of 48% aqueous hydrobromic acid was refluxed at 150° C. for 90 minutes and then cooled to room temperature. The mixture was extracted with methylene chloride and the organic phase was dried over sodium sulfate, filtered and concentrated to dryness under reduced pressure to obtain 8.55 g of residue which was chromatographed on silica (eluant: methylene chloride - tetrahydrofuran 1-1) to obtain 3.2 g of product. The product was dissolved in 3 ml of hot isopropanol and crystallized at room temperature. The product was filtered, washed twice with 3 ml of iced isopropanol and dried under reduced pressure at 50° C. to obtain 1.72 g of the desired product melting at 82°-84° C.

Analysis: $C_{21}H_{29}NO$; molecular weight = 311.471
Calculated: %C 80.98, %H 9.38, %N 4.49,
Found: 81.20, 9.60, 4.40

EXAMPLE 2

N-pentyl-N-phenethyl-N-3-hydroxyphenethylamine hydrochloride 4 ml of concentrated hydrochloric acid were added to a mixture of 15 g of the product of Example 1 and 45 ml of water and the suspension was stirred overnight at room temperature. The mixture was cooled to 0° C. to 5° C. for one hour and was vacuum filtered. The product was rinsed with 35 ml of iced water at 5° C. and was dried to obtain 16.29 g of the hydrochloride melting at 115° C.

Analysis: $C_{21}H_{30}NOCl$; molecular weight = 347.93
Calculated: %C 72.5 %H 8.69, %N 4.03, %Cl 10.19,
Found: 72.7, 8.8, 3.9, 10.3

EXAMPLE 3

Tablets were prepared containing 100 mg of the product of Example 1 and sufficient excipient of lactose, talc, starch and magnesium stearate for a final weight of 400 mg.

EXAMPLE 4

An injectable solute (intra-muscular route) was prepared containing 50 mg of the product of Example 1 and sufficient sterile solvent for a volume of 5 ml.

PHARMACOLOGICAL STUDY

1) Antagonist effect vis-a-vis the diuretic activity of U-50488 Action on diuresis The test was carried out on male rats with an average body weight of 150 g having gone without food for 16 hours but having drinking water and libitum. The product of Example 1 was administered at 20 mg/kg (SC route) and U-50488 at 5 mg/kg orally collected for one hour. The results were as follows:

|  | Dose mg/kg SC | Volume of urine excreted in 1 hour (ml/kg) m ± esm |
|---|---|---|
| Controls | 0 | 6.5 ± 0.2 |
| Product of example 1 | 20 | 6.7 ± 0.2 |
| U-50448 | 5 | 9.8 ± 0.3 |
| U-50488 + product of example 1 | 5 + 20 | 5.7 ± 0.2 |

2) Antagonist effect vis-a-vis the analgesic activity of U-50488 Hot plate test with mice Female mice were placed individually on a copper plate maintained at 56° C. using a thermostatically-controlled water bath. Reaction to pain was shown by the licking of one or both of the front paws. The reaction time to the thermal stimulus was noted and only animals reacting in 4.5 to 6.5 seconds were retained. Then the animals were divided into homogeneous groups. A group of control animals received the U-50488 at 5 mg/kg SC, another group received the product of Example 1 at 20 mg/kg, while the two products were administered simultaneously subcutaneously to a third group of animals at these same doses. A group of control animals received injections of the corresponding vehicle. The reaction time to the pain was measured thirty minutes after injection of the products and the variations in reaction times were expressed as a percentage of the initial time, taking into account the variation in the control group.

|  | Dose mg/kg SC | Reaction time (s) m ± esm | |
|---|---|---|---|
|  |  | 0 mn | 30 mn |
| Controls | 0 | 5.2 ± 0.1 | 5.0 ± 0.2 |
| Product of example 1 | 20 | 5.1 ± 0.1 | 4.7 ± 0.6 |
| U-50488 | 5 | 5.2 ± 0.1 | 9.6 ± 1.1 |
| U-50488 + product of example 1 | 5 + 20 | 5.1 ± 0.2 | 6.7 ± 0.6* |

*p <0.05 according to the Student test relative to a group treated with U-50488.

3) Evidence of the property of dissociation of kappa, mu and dopaminergic activities or the sole affinity for the kappa opiate receptor:

a) Test of the bonding to the kappa opiate receptor in vitro

Membrane samples prepared from the cerebellum of guinea pigs preserved at −30° C. (optionally for about 30 days) were used.

These samples were suspended in pH 7.7 Tris buffer. Fractions of 2 ml were allocated into hemolysis tubes and 1 nM of 3H ethylketocyclazocine and the product to be studied were added. The product was first tested in triplicate at $5 \times 10^{-6}$ M. When the tested product displaced more than 50% of the radioactivity bonded specifically to the receptor, it was tested again according to a range of 7 doses to determine the dose which inhibited 50% of the radioactivity bonded specifically to the receptor. Thus, the 50% inhibiting concentration was determined.

The non-specific bonding was determined by the addition of product known under the name U-50 488 H (Lahti et al. 1982, Life Sci. Vol. 31, p. 2257) at $10^{-5}$ M in triplicate. Incubation took place at 25° C. for 40 minutes, followed by returning to the water bath at 0° C. for 5 minutes, then vacuum filtering, rinsing with pH 7.7 Tris buffer, and the radioactivity was counted in the presence of a Triton scintillator. The result was expressed directly as the 50% inhibiting concentration ($IC_{50}$), that is to say as the concentration of studied product, expressed in nM, necessary to displace 50% of the radioactivity specifically bonded to the studied receptor. The $IC_{50}$ for the product of Example 1 was 57 nanomoles.

b) Test of bonding to the mu opiate receptor in vitro

Membrane samples preserved at −30° C. (optionally for about 30 days) from the brains of rats were used. These samples were suspended in pH 7.7 Tris buffer and 2 ml Fractions were allocated onto hemolysis tubes and $^3$H DAGO (1 nM) and the product to be tested were added. The product was first tested in triplicate at $5 \times 10^{-5}$ M. When the tested product displaced more than 50% of the radioactivity specifically bonded to the receptor, it was tested again according to a range of 7 doses to determine the dose which inhibited 50% of the radioactivity specifically bonded to the receptor. In this way, the 50% inhibiting concentration was determined.

The non-specific bonding was determined by the addition of morphine (CHILDERS. Eur. J. Pharmacol. Vol. 55, p. 11) at $10^{-5}$ (in triplicate). Incubation took place at 25° C. for 40 minutes, followed by returning to the water bath at 0° C. for 5 minutes, then vacuum filtering, rinsing with pH 7.7 Tris buffer and the radioactivity was counted in the presence of a Triton scintillator. The results was expressed directly as the 50% inhibiting concentration ($IC_{50}$), that is to say the concentration of studied product, expressed in nM, necessary to displace 50% of the radioactivity specifically bonded to the studied receptor. The $IC_{50}$ for the product of Example 1 was 840 nanomoles.

c) Test of bonding to the dopamine receptor in vitro

Membrane samples preserved at −30° C. (optionally for about 30 days) and prepared from the striated bodies of rats were used. The samples were suspended in pH 7.25 Krebs Tris buffer. After a pre-incubation of 10 minutes at 37° C., 2 ml fractions were allocated into hemolysis tubes and $^3$H spiroperidol (0.15 nM) and the product to be studied was added. The product was first tested at $5 \times 10^{-6}$M, in triplicate. When the tested product displaced more than 50% of the radioactivity specifically bonded to the receptor, it was tested again according to a range of 7 doses to determine the dose which inhibited 50% of the radioactivity specifically bonded to the receptor. In this way, the 50% inhibiting concentration was determined.

The non-specific bonding was determined by the addition of haloperidol (SIELDS et al BRAIN RESEARCH; 1977 Vol. 136, p. 578 to 584) at $10^{-5}$M in triplicate. Incubation took place at 27° C. for 20 minutes, followed by returning to the water bath at 0° C. for 5 minutes, then vacuum filtering, rinsing with pH 7.7 Tris buffer, and the radioactivity was counted in the presence of a Triton scintillator. The result was expressed directly as the 50% inhibiting concentration, that is to say the concentration of the product studied, expressed in nM, necessary to displace 50% of the radioactivity specifically bonded to the studied receptor. The $IC_{50}$ for the product of Example 1 was 10,600 nanomoles.

CONCLUSION

The product of Example 1 only has an affinity for the kappa opiate receptor.

4) Test for distinction between agonist and antagonist on the kappa opiate receptor The use of an antagonist ligand allows the distinguishing in vitro as to whether a product is agonist or antagonist. In this case, in effect, the $IC_{50}$ of an agonist will increase to a significant extent (15 to 50) according to whether it is incubated in the absence or presence of NaCl and/or GTP, while the $IC_{50}$ of an antagonist will vary little over the 2 conditions.

Membrane samples preserved at −30° C. (optionally for about 30 days) prepared from the cerebellum of guinea pigs, with or without NaCl 100 mM, GTP 50 uM are used. These samples were suspended in pH 7.7 Tris buffer 50 nM and 2 ml fractions were allocated in to hemolysis tubes and $^3$H diprenorphine (0.3 nM) and the product to be studied was added. The product was first tested at $5 \times 10^{-6}$M, in triplicate. When the tested product displaced more than 50% of the radioactivity specifically bonded to the receptor, it was tested again over a range of 7 doses to determine the dose which inhibited 50% of the adioactivity specifically bonded to the receptor. In this way, the 50% inhibiting concentration was determined.

The non-specific bonding was determined by the addition of a product called U-50488 (FRANCES et al Eur. J. Pharmacol. 1985, Vol. 117, p. 223) at $10^{-5}$M in triplicate. Incubation took place at 25° C. for 40 minutes, followed by returning to the water bath at 0° C. for 5 minutes, then vacuum filtering, rinsing in pH 7.7 Tris buffer and counting the radioactivity in the presence of a Triton scintillator. The results were expressed directly as the 50% inhibiting concentration ($IC_{50}$), that is to say the of the studied product, expressed in nM, necessary to displaced 50% of the radioactivity specifically bonded to the studied receptor. The $IC_{50}$ was 43 nM in the absence of GTP and NaCl, and 135 nM in the presence of GTP and NaCl. Therefore the result shows clearly that the product of Example 1 is an antagonist product of the kappa receptor.

Various modifications of the product and method of the invention may be made without departing from the spirit or scope thereof and it is to be understood that the invention is intended to be limited only as defined in the appended claims.

What is claim is:

1. A compound selected from the group consisting of a compound of the formula

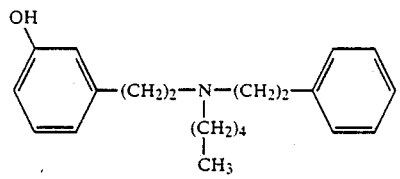

and its non-toxic, pharmaceutically acceptable acid addition salts.

2. A compound of claim 1 which is N-pentyl-N-phenethyl-3-hydroxy phenethylamine.

3. A compound of claim 1 which is N-pentyl-N-phenethyl-3-hydroxy phenethylamine hydrochloride.

4. A compound of the formula

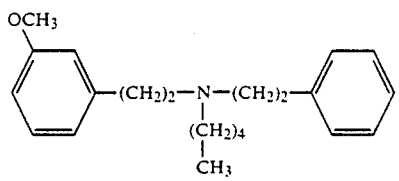

5. A composition for inducing dissociated antagonist affinity for the kappa opiate receptor comprising an amount of a compound of claim 1 sufficient to induce dissociated antagonist affinity for the kappa opiate receptor and an inert pharmaceutical carrier.

6. A method for treating an overdosing of an agonist product of the kappa opiate receptor in warm-blooded animals comprising administering to warm-blooded animals an amount of a compound of claim 1 sufficient to treat said overdose.

* * * * *